United States Patent
Choi

(10) Patent No.: US 12,039,697 B2
(45) Date of Patent: Jul. 16, 2024

(54) METHOD AND SYSTEM FOR RECONSTRUCTING HIGH RESOLUTION VERSIONS OF LOW RESOLUTION IMAGES OF A CINE LOOP SEQUENCE

(71) Applicant: GE Precision Healthcare LLC, Wauwatosa, WI (US)

(72) Inventor: Jaehyeok Choi, Seoul (KR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 253 days.

(21) Appl. No.: 17/473,018

(22) Filed: Sep. 13, 2021

(65) Prior Publication Data

US 2023/0084230 A1 Mar. 16, 2023

(51) Int. Cl.
| | |
|---|---|
| G06T 3/4053 | (2024.01) |
| A61B 8/00 | (2006.01) |
| A61B 8/08 | (2006.01) |
| G16H 30/20 | (2018.01) |

(52) U.S. Cl.
CPC ............ *G06T 3/4053* (2013.01); *A61B 8/461* (2013.01); *A61B 8/469* (2013.01); *A61B 8/5207* (2013.01); *A61B 8/5269* (2013.01); *G16H 30/20* (2018.01); *G06T 2210/41* (2013.01)

(58) Field of Classification Search
CPC .................... G06T 3/40; G06T 3/4053; G06T 2207/10132; G06T 2207/10072; G06T 2207/10016; G06T 2210/41; G16H 30/20; A61B 8/5207; A61B 8/5269
See application file for complete search history.

(56) References Cited

U.S. PATENT DOCUMENTS

| | | | |
|---|---|---|---|
| 11,559,284 B2 * | 1/2023 | Lundberg | A61B 8/5207 |
| 2016/0173770 A1 | 6/2016 | Fosodeder et al. | |
| 2016/0260198 A1 * | 9/2016 | Hu | G06T 3/4053 |
| 2018/0137603 A1 | 5/2018 | Hsiao et al. | |

FOREIGN PATENT DOCUMENTS

EP            3505069 A1      7/2019

* cited by examiner

*Primary Examiner* — Antonio A Caschera
(74) *Attorney, Agent, or Firm* — McAndrews, Held & Malloy, Ltd.; Daniel Bissing; David Bates

(57) ABSTRACT

Systems and methods for reconstructing high resolution versions of low resolution cine sequence images include acquiring a low resolution cine sequence, receiving a user input stopping the acquisition of the cine sequence, and initiating acquisition of a high resolution image. The systems and methods include iteratively reconstructing a high resolution version of each of the low resolution images in the cine sequence in reverse, beginning with a last acquired low resolution image and ending with a first acquired low resolution image. The high resolution version of the last acquired low resolution image is reconstructed based on the last acquired low resolution image and the high resolution image. The high resolution version of each of the low resolution images prior to the last acquired low resolution image is iteratively reconstructed based on a respective low resolution image and the high resolution version of a subsequently acquired low resolution image.

20 Claims, 4 Drawing Sheets

METHOD AND SYSTEM FOR RECONSTRUCTING HIGH RESOLUTION VERSIONS OF LOW RESOLUTION IMAGES OF A CINE LOOP SEQUENCE

FIELD

Certain embodiments relate to ultrasound imaging. More specifically, certain embodiments relate to a method and system for reconstructing high resolution versions of low resolution images of a cine loop sequence.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Conventional ultrasound image acquisitions involve a trade-off between frame rates and line densities. For example, line densities are typically increased by increasing the number of lines, which reduces the frame rate. As another example, frame rates are typically increased by decreasing the number of lines, which reduces the line densities. In the case of real-time B-mode ultrasound image scanning, an ultrasound operator may freeze scanning to focus on a paused ultrasound image or a cine loop sequence to perform medical diagnosis and/or measurements.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for reconstructing high resolution versions of low resolution images of a cine loop sequence, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
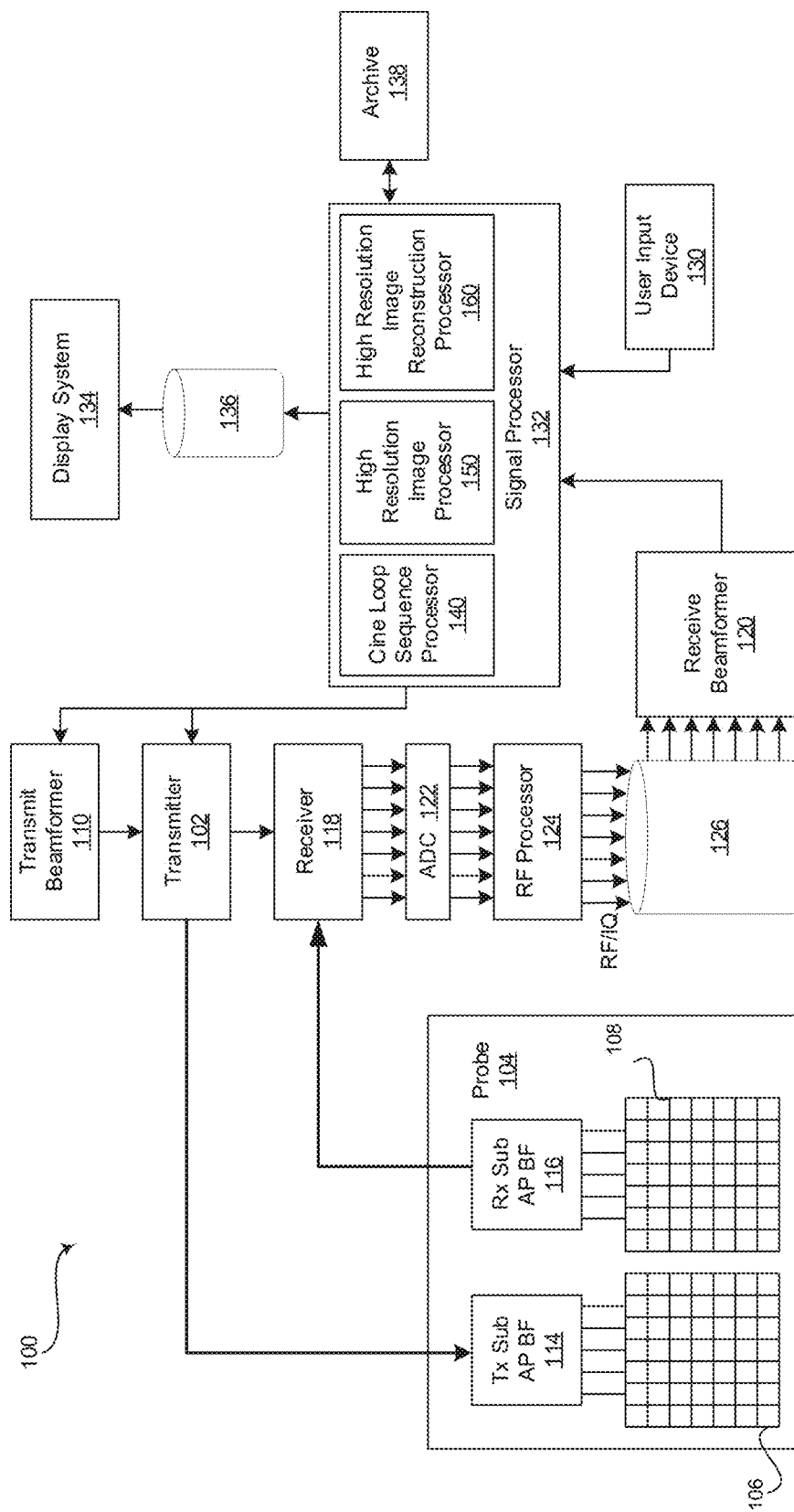
FIG. 1 is a block diagram of an exemplary ultrasound system that is operable to reconstruct high resolution versions of low resolution images of a cine loop sequence, in accordance with various embodiments.

Certain embodiments may be found in a method and system for reconstructing high resolution versions of low resolution images of a cine loop sequence. Various embodiments have the technical effect of acquiring and presenting a high resolution image in response to a user input stopping a low resolution cine loop sequence acquisition. Aspects of the present disclosure have the technical effect of iteratively reconstructing high resolution versions of each of the low resolution images in a series of sequentially acquired low resolution images (i.e., cine loop sequence) in reverse, beginning with a last acquired low resolution image and ending with a first acquired low resolution image. The high resolution version of the last acquired low resolution image may be reconstructed based on the last acquired low resolution image and the high resolution image. The high resolution version of each of the low resolution images prior to the last acquired low resolution image may be iteratively reconstructed based on a respective low resolution image and the high resolution version of a subsequently acquired low resolution image in the series of sequentially acquired low resolution images.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, MGD, and/or sub-modes of B-mode and/or CF such as Volume Compound Imaging (VCI), Shear Wave Elasticity Imaging (SWEI), TVI, Angio, B-flow, BMI, BMI_Angio, and in some cases also MM, CM, TVD, CW where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to reconstruct high resolution versions of low resolution images of a cine loop sequence, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements or may be a mechanical one dimensional (1D) array, among other things. The ultrasound probe 104 may comprise a group of transmit transducer elements 106 and a group of receive transducer elements 108, that normally constitute the same elements. In certain embodiments, the ultrasound probe 104 may be operable to acquire ultrasound image data covering at least a substantial portion of an anatomy, such as a heart, a fetus, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, input low resolution image acquisition parameters, input low resolution image processing parameters, input high resolution image acquisition parameters, input high resolution image processing parameters, modify settings, select protocols and/or templates, change scan mode, navigate acquired ultrasound images, manipulate tools for reviewing acquired ultrasound data, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a cine loop sequence processor 140, a high resolution image processor 150, and a high resolution image reconstruction processor 160 and may be capable of receiving input information from a user input device 130 and/or archive 138, generating an output displayable by a display system 134, and manipulating the output in response to input information from a user input device 130, among other things. The signal processor 132, cine loop sequence processor 140, high resolution image processor 150, and high resolution image reconstruction processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a cine loop sequence processor 140 that comprises suitable logic, circuitry, interfaces and/or code that may be operable to apply low resolution image acquisition parameters to the ultrasound system 100 for acquisition of a real-time scan (i.e., cine loop sequence) and to process the acquired low resolution images of the real-time scan based on low resolution image processing parameters. For example, the ultrasound system 100 may acquire a cine loop sequence based on low resolution image acquisition parameters applied by the cine loop sequence processor 140. The low resolution image acquisition parameters may be default parameters and/or parameters provided by a user via the user input device 130. The low resolution cine loop sequence acquired by the ultrasound system 100 may be stored at a cine buffer. The cine loop sequence processor 140 may be configured to process the acquired low resolution images to create the cine loop sequence based on low resolution image processing parameters, which may be default parameters and/or parameters provided by the user via the user input device 130. The cine loop sequence comprises a plurality of low resolution images that may be presented at the display system 134 and/or stored in archive 138 or any suitable data storage medium. The cine loop sequence may be defined and stored based on a user input (e.g., scan freeze input) received by the signal processor 132. For example, the cine loop sequence may be defined as the low resolution image frames acquired in the 5 seconds, or any suitable amount of time, prior to receiving the user input (e.g., scan freeze input) stopping the acquisition of the low resolution cine loop sequence.

The signal processor 132 may include a high resolution image processor 150 that comprises suitable logic, circuitry, interfaces and/or code that may be operable to apply high resolution image acquisition parameters to the ultrasound system 100 for acquisition of a high resolution image and to process the acquired high resolution image based on high resolution image processing parameters. For example, in response to receiving the user input (e.g., scan freeze input) stopping the acquisition of the low resolution cine loop sequence, the ultrasound system 100 may acquire a high resolution image based on high resolution image acquisition parameters applied by the high resolution image processor 150. The high resolution image acquisition parameters include a line density acquisition parameter that is greater than a line density acquisition parameter of the low resolution image acquisition parameters. The high resolution image acquisition parameters may be default parameters and/or parameters provided by a user via the user input device 130. The high resolution image acquired by the ultrasound system 100 may be stored at a cine buffer. The high resolution image processor 150 may be configured to process the acquired high resolution image based on high resolution image processing parameters, which may be default parameters and/or parameters provided by the user via the user input device 130. The high resolution image may be presented at the display system 134 and/or stored in archive 138 or any suitable data storage medium in response to receiving the user input (e.g., scan freeze) stopping the acquisition of the low resolution cine loop sequence and initiating the acquisition of the high resolution image.

Figure 2:
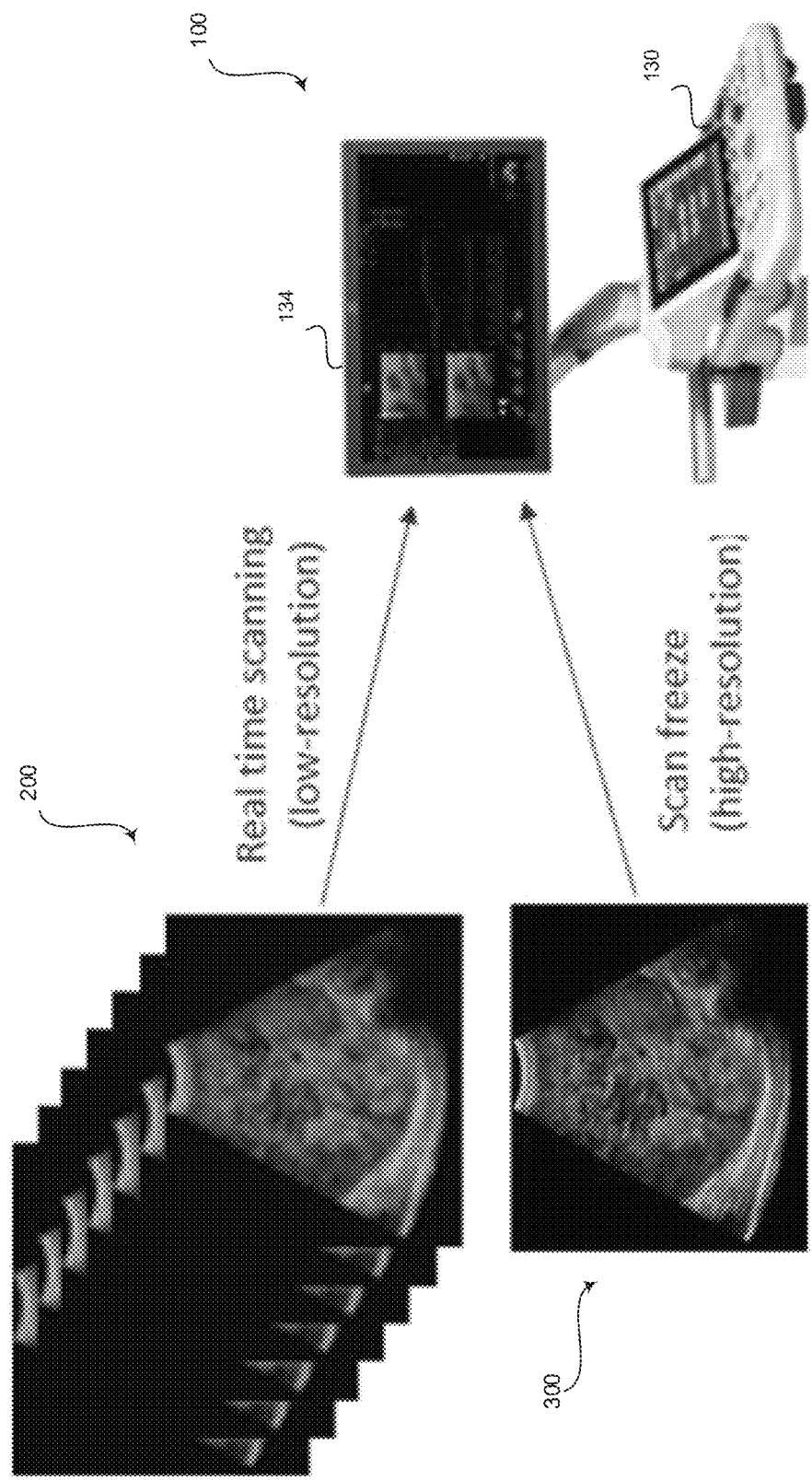
FIG. 2 illustrates an exemplary low resolution cine loop sequence presented at a display system of an ultrasound system followed by a high resolution acquisition presented at the display system, the high resolution acquisition performed and presented in response to a user input stopping the low resolution cine loop sequence acquisition, in accordance with various embodiments.

FIG. 2 illustrates an exemplary low resolution cine loop sequence 200 presented at a display system 134 of an ultrasound system 100 followed by a high resolution acquisition 300 presented at the display system 134, the high resolution acquisition 300 performed and presented in response to a user input stopping the low resolution cine loop sequence acquisition, in accordance with various embodiments. Referring to FIG. 2, an ultrasound system 100 comprising a display system 134 and user input device 130 is shown. The ultrasound system 100 may share various characteristics with the ultrasound system 100 of FIG. 1. The ultrasound system 100 acquires a low resolution cine loop sequence 200 comprising a plurality of low resolution frames. The cine loop sequence 200 may be acquired and presented at the display system 134 according to low resolution image acquisition parameters. The ultrasound system 100 may be configured to receive a user input (e.g., scan freeze) stopping the acquisition of the low resolution cine loop sequence and initiating the acquisition of a high resolution image 300. The high resolution image 300 may be acquired and presented at the display system 134 according to high resolution image acquisition parameters. The high resolution image acquisition parameters includes a line density parameter that is greater than the line density parameter of the low resolution image acquisition parameters.

Referring again to FIG. 1, the signal processor 132 may include a high resolution image reconstruction processor 160 that comprises suitable logic, circuitry, interfaces and/or code that may be operable to reconstruct high resolution versions of each of the low resolution images in the cine loop sequence. For example, the high resolution image reconstruction processor 160 may execute a super-resolution algorithm to reconstruct the high resolution versions of the low resolution images in the cine loop sequence. The super-resolution algorithm may include machine learning algorithms, artificial intelligence (e.g., neural network(s)), and/or any suitable image reconstruction techniques. The super-resolution algorithm executed by the high resolution image reconstruction processor 160 receives a high resolution image and a low resolution image of the cine loop sequence as an input. The super-resolution algorithm executed by the high resolution image reconstruction processor 160 maps anatomical structures in the high resolution image to corresponding anatomical structures in the low resolution image to identify corresponding pixels or groups of pixels in the high and low resolution images. The super-resolution algorithm executed by the high resolution image reconstruction processor 160 adds image pixels and image pixel values to the low resolution image based on the corresponding image pixels and pixel values in the high resolution image as mapped to generate a high resolution version of the low resolution image. The super-resolution algorithm executed by the high resolution image reconstruction processor 160 may compare the high resolution version with the original high resolution image acquired by the ultrasound system 100 to identify and remove artifacts from the high resolution version generated by the super-resolution algorithm.

In various embodiments, the super-resolution algorithm executed by the high resolution image reconstruction processor 160 may be provided as a deep neural network that may be made up of, for example, an input layer, an output layer, and one or more hidden layers in between the input and output layers. Each of the layers may be made up of a plurality of processing nodes that may be referred to as neurons. For example, the high resolution image reconstruction processor 160 may include an input layer having a neuron for each pixel or a group of pixels from the high resolution image and the low resolution image of the cine loop sequence. The output layer may have neurons corresponding to a reconstructed high resolution version of the low resolution image of the cine loop sequence. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The neurons of a fourth layer may learn to map anatomical structures in the high resolution image to anatomical structures in the low resolution image to identify corresponding pixels or groups of pixels in the high and low resolution images. The neurons of a fifth layer may add image pixels and image pixel values to the low resolution image based on the corresponding image pixels and pixel values in the high resolution image as mapped to generate a high resolution version of the low resolution image. The neurons of a sixth layer may compare the high resolution version with the original high resolution image acquired by the ultrasound system 100 to identify and remove artifacts from the high resolution version generated by the super-resolution algorithm. The processing performed by the high resolution image reconstruction processor 160 deep neural network (e.g., convolutional neural network) may reconstruct high resolution versions of low resolution images of a cine loop sequence with a high degree of probability. The high resolution image reconstruction processor 160 deep neural network may be trained by a training system (not shown) comprising a training engine and a training database. The training engine may comprise suitable logic, circuitry, interfaces and/or code that may be operable to train the neurons of the deep neural network(s) (e.g., artificial intelligence model(s)) inferenced (i.e., deployed) by the high resolution image reconstruction processor 160. For example, the artificial intelligence model inferenced by the high resolution image reconstruction processor 160 may be trained to reconstruct high resolution versions of low resolution frames of a cine loop sequence. As an example, the training engine may train the deep neural networks deployed by the high resolution image reconstruction processor 160 using database(s) of classified images. In various embodiments, the training engine and/or training databases may be remote system(s) communicatively coupled via a wired or wireless connection to the ultrasound system 100. Additionally and/or alternatively, components or all of the training system may be integrated with the ultrasound system 100 in various forms.

The high resolution image reconstruction processor 160 may comprise suitable logic, circuitry, interfaces and/or code that may be operable to reconstruct high resolution versions of each of the low resolution images in the cine loop sequence in reverse, beginning with a last acquired low resolution image and ending with a first acquired low resolution image. For example, the high resolution version of the last acquired low resolution image is reconstructed based on the last acquired low resolution image and the acquired high resolution image. The high resolution version of each of the low resolution images prior to the last acquired low resolution image is iteratively reconstructed based on a respective low resolution image and the high resolution version of a subsequently acquired low resolution image in the series of sequentially acquired low resolution images of the cine loop sequence.

Figure 3:
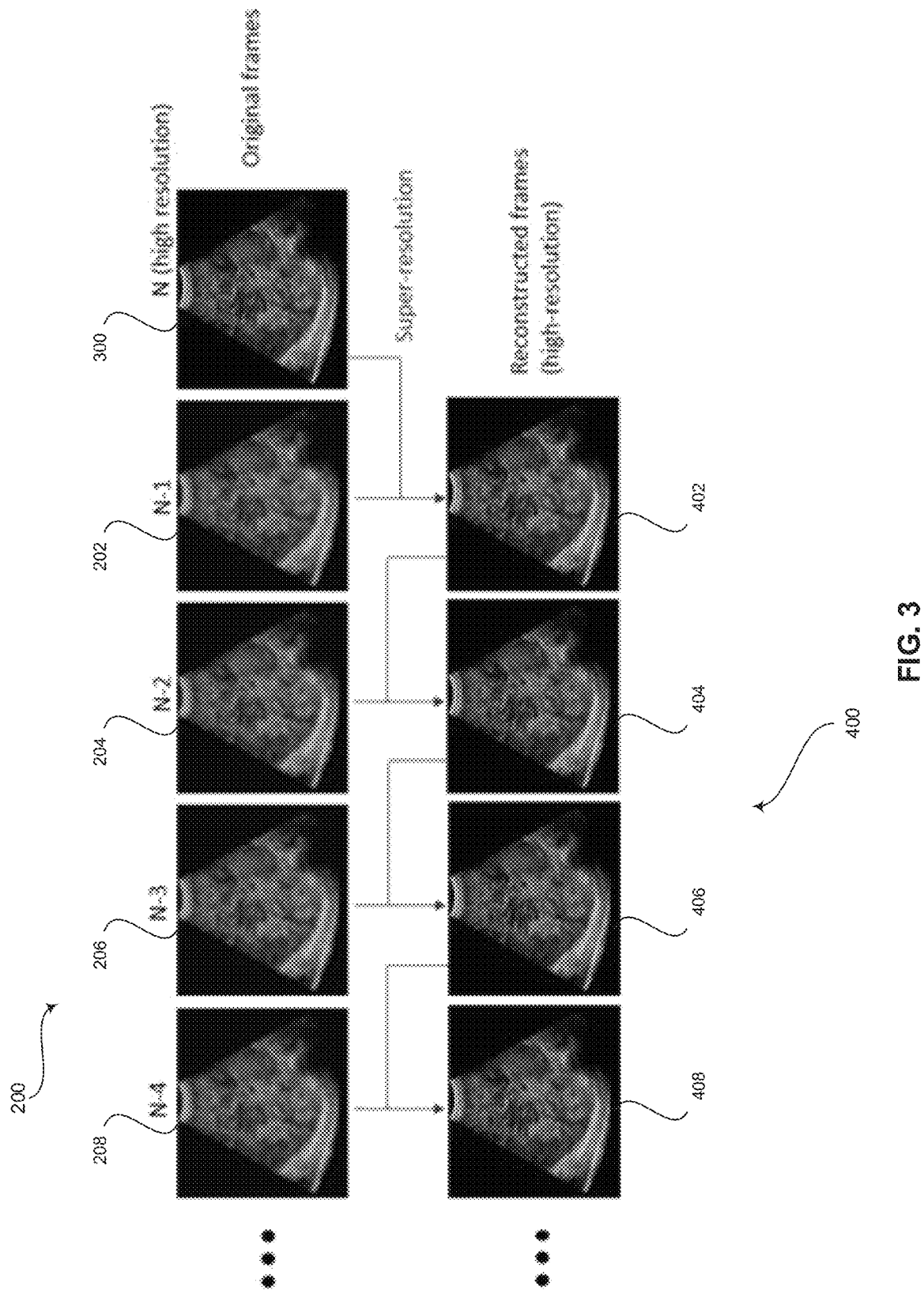
FIG. 3 illustrates exemplary iterative reconstruction of high resolution versions of each of the low resolution images in a series of sequentially acquired low resolution images in reverse, beginning with a last acquired low resolution image and ending with a first acquired low resolution image, in accordance with various embodiments.

FIG. 3 illustrates exemplary iterative reconstruction of high resolution versions 402-408 of each of the low resolution images 202-208 in a series 200 of sequentially acquired low resolution images in reverse, beginning with a last acquired low resolution image 202 and ending with a first acquired low resolution image 208, in accordance with various embodiments. Referring to FIG. 3, a low resolution cine loop sequence 200 is acquired until a user input (e.g., scan freeze) is received stopping the cine loop sequence acquisition and initiating acquisition of a high resolution image 300. The low resolution cine loop sequence 200 comprises a plurality of low resolution images 202-208. The last (N−1) low resolution image 202 is reconstructed by the high resolution image reconstruction processor 160 executing a super-resolution algorithm that receives the low resolution image 202 and the high resolution image 300 as an input, and outputs the reconstructed high resolution version 402. The reconstructed high resolution version 402 and the prior (N−2) low resolution image 204 are used by the high resolution image reconstruction processor 160 executing the super-resolution algorithm to generate high resolution version 404 of the low resolution image 204. The reconstructed high resolution version 404 and the prior (N−3) low resolution image 206 are used by the high resolution image reconstruction processor 160 executing the super-resolution algorithm to generate high resolution version 406 of the low resolution image 206. The reconstructed high resolution version 406 and the prior (N−4) low resolution image 208 are used by the high resolution image reconstruction processor 160 executing the super-resolution algorithm to generate high resolution version 408 of the low resolution image 208. The iterative reconstruction of high resolution versions 402-408 of each of the low resolution images 202-208 in a series 200 of sequentially acquired low resolution images in reverse continues until the first acquired low resolution image 208 is reconstructed as a high resolution version 408 of the first acquired low resolution image 208.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present low resolution cine loop sequences 200, a high resolution image 300, reconstructed high resolution versions 402-408 of low resolution images 202-208 of a cine loop sequence 200, a high resolution version of the cine loop sequence 400, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores low resolution cine loop sequences 200, low resolution images 202-208, a high resolution image 300, a high resolution version of the cine loop sequence 400, reconstructed high resolution versions 402-408 of low resolution images 202-208 of a cine loop sequence 200, and instructions for reconstructing high resolution versions 402-408 of low resolution images 202-208 of a cine loop sequence 200, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 4:
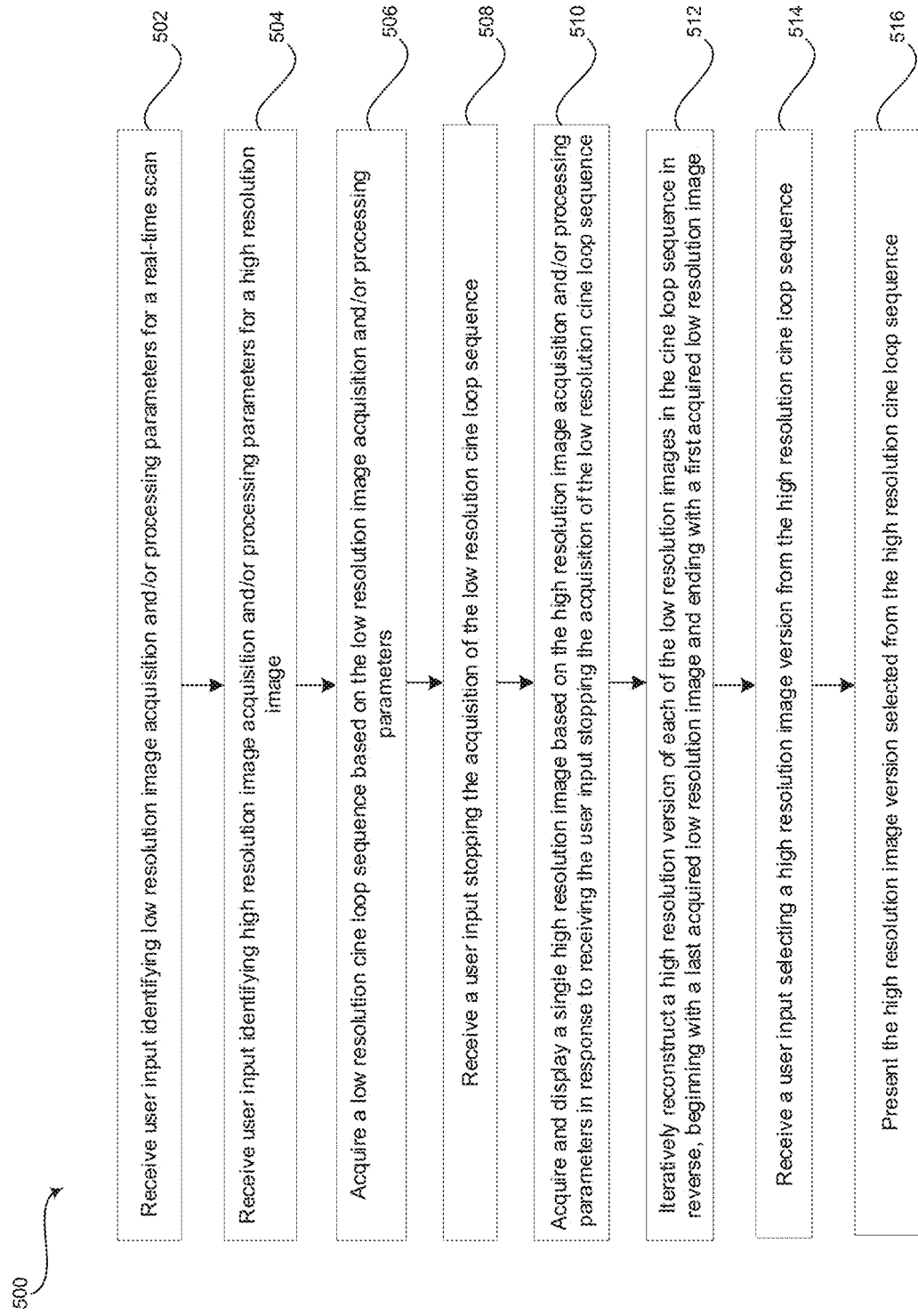
FIG. 4 is a flow chart illustrating exemplary steps for reconstructing high resolution versions of low resolution images of a cine loop sequence, in accordance with various embodiments.

FIG. 4 is a flow chart 500 illustrating exemplary steps 502-516 for reconstructing high resolution versions 402-408 of low resolution images 202-208 of a cine loop sequence 200, in accordance with various embodiments. Referring to FIG. 4, there is shown a flow chart 500 comprising exemplary steps 502 through 516. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, a user input may be received via the user input device 130 identifying low resolution image acquisition and/or processing parameters for a real-time scan. The acquisition imaging parameters may include various settings for line density, depth, width, position of a region-of-interest (ROI), pulse-repetition-frequency (PRF), gain, adaptive gain, transmit focus position, or some combination of settings optimized for a low resolution cine loop sequence acquisition. The low resolution processing parameters may include, for example, a low sampling rate, a low dynamic range, a high persistence filter setting, and other processing settings optimized for low resolution cine loop sequence processing. The low resolution image acquisition and/or processing parameters may be stored in association with the low resolution cine loop sequence scan mode and applied when acquiring and processing a cine loop sequence 200 comprising a plurality of low resolution frames 202-208 for display at a display system 134. In various embodiments, one or more of the low resolution image acquisition and/or processing parameters may be default parameters that may be optionally changed via the user input device 130

At step 504, a user input may be received via the user input device 130 identifying high resolution image acquisition and/or processing parameters for a high resolution image 300. The high resolution image acquisition parameters may include various settings for line density, depth, width, position of a region-of-interest (ROI), pulse-repetition-frequency (PRF), gain, adaptive gain, transmit focus position, or some combination of settings optimized for a high resolution image acquisition. The high resolution image processing parameters may include, for example, a high sampling rate, a high dynamic range, a low persistence filter setting, and other processing settings optimized for high resolution image processing. The high resolution image acquisition and/or processing parameters generate a high resolution image 300 with greater resolution than low resolution images 202-208 in the cine loop sequence 200 acquired and processed according to the low resolution image acquisition and/or processing parameters. In an exemplary embodiment, one or more of the high resolution image acquisition and/or processing parameters may be default parameters that may be optionally changed via the user input device 130.

At step 506, the ultrasound system 100 acquires a low resolution cine loop sequence 200 based on the low resolution image acquisition parameters. The ultrasound system 100 acquires the low resolution cine loop sequence 200 using the stored low resolution image acquisition parameters that can be default parameters and/or parameters obtained at step 502 above. The cine loop sequence processor 140 of the signal processor 132 processes the low resolution images 202-208 to create a low resolution cine loop sequence 200 based on the low resolution image processing parameters. The low resolution cine loop sequence 200 comprises a plurality of low resolution images 202-208. The low resolution cine loop sequence 200 may be presented at a display system 134 and/or stored at archive 138 and/or any suitable data storage medium.

At step 508, the ultrasound system 100 receives a user input via the user input device 130 to stop the acquisition of the low resolution cine loop sequence 200. The user input can be a button, switch, or any suitable mechanism that may be activated by a user (e.g., scan freeze) to stop the low resolution cine loop sequence acquisition and initiate acquisition of a high resolution image 300 at step 510.

At step 510, the ultrasound system 100 acquires and displays a single high resolution image 300 based on the high resolution image acquisition and/or processing parameters in response to receiving the user input stopping the acquisition of the low resolution cine loop sequence 200. The ultrasound system 100 acquires the high resolution image 300 based on the stored high resolution image acquisition and/or processing parameters that can be default parameters and/or parameters obtained at step 504 above. The high resolution image processor 150 of the signal processor 132 processes the high resolution image 300 based on the high resolution image processing parameters and presents the high resolution image 300 at display system 134. The high resolution image 300 is processed and displayed at a resolution that is greater than the resolution of the low resolution images 202-208 of the cine sequence 200. The high resolution image 300 may be stored at archive 138 and/or any suitable data storage medium.

At step 512, the signal processor 132 iteratively reconstructs a high resolution version 402-408 of each of the low resolution images 202-208 in the cine loop sequence 200 in reverse, beginning with a last acquired low resolution image 202 and ending with a first acquired low resolution image 208. For example, a high resolution image reconstruction processor 160 of the signal processor 132 may be configured to reconstruct a high resolution version 402 of the last acquired low resolution image 202 based on the last acquired low resolution image 202 and the acquired high resolution image 300. A high resolution version 404-408 of each of the low resolution images 204-208 prior to the last acquired low resolution image 202 is iteratively reconstructed based on a respective low resolution image 204-208 and the high resolution version 402-406 of a subsequently acquired low resolution image 202-206 in the series of sequentially acquired low resolution images 202-208 of the cine loop sequence 200. The process is performed iteratively in reverse until high resolution versions 402-408 all of the low resolution images 202-208 of the cine loop sequence 200 have been reconstructed, resulting in a high resolution cine loop sequence 400. In various embodiments, the high resolution image 300 may be included in the high resolution cine loop sequence 400 as the last high resolution image in the sequence of high resolution images. The high resolution cine loop sequence 400 may be presented at the display system 134 and/or stored at archive 138 and/or any suitable data storage medium.

At step 514, the ultrasound system 100 receives a user input via user input device 130 selecting a high resolution image version 402-408 from the high resolution cine loop sequence 400. For example, the signal processor 132 may receive a user input via the user input device 130 selecting a different high resolution image version 402-408 to view in the reconstructed high resolution cine loop sequence 400.

At step 516, the signal processor 132 presents the high resolution image version 402-408 selected from the high resolution cine loop sequence 400. For example, the high resolution image version 402-408 corresponding with the low resolution image 202-208 of the low resolution cine loop sequence 200 is presented at the display system 134 in response to the user input received at step 514, such that the ultrasound operator may review the high resolution versions 402-408 of the acquired low resolution images 202-208 of the low resolution cine loop sequence 200.

Aspects of the present disclosure provide a method 500 and system 100 for reconstructing high resolution versions 402-408 of low resolution images 202-208 of a cine loop sequence 200. In accordance with various embodiments, the method 500 may comprise acquiring 506, by a medical imaging modality, a low resolution cine loop sequence 200 comprising a series of sequentially acquired low resolution images 202-208. The method 500 may comprise receiving 508, by at least one processor 132,140, 150, a user input stopping the acquisition of the low resolution cine loop sequence 200. The method 500 may comprise acquiring 510, by the medical imaging modality, a single high resolution image 300 in response to the receiving the user input stopping the acquisition of the low resolution cine loop sequence 200. The method 500 may comprise iteratively reconstructing 512, by the at least one processor 132,160, a high resolution image version 402-408 of each of the low resolution images 202-208 in the series of sequentially acquired low resolution images 200 in reverse, beginning with a last acquired low resolution image 202 and ending with a first acquired low resolution image 208, to generate a high resolution cine loop sequence 400. The high resolution image version 402 of the last acquired low resolution image 202 is reconstructed based on the last acquired low resolution image 202 and the single high resolution image 300. The high resolution image version 404-408 of each of the low resolution images 204-208 prior to the last acquired low resolution image 202 is iteratively reconstructed based on a respective low resolution image 204-208 and the high resolution image version 402-406 of a subsequently acquired low resolution image 202-206 in the series of sequentially acquired low resolution images 200. The method 500 may comprise receiving 514, by the at least one processor 132, a user navigation input selecting a high resolution image version 402-408 from the high resolution cine loop sequence 400. The method 500 may comprise causing a display system 134 to present 516, by the at least one processor 132, 160, the high resolution image version 402-408 based on the user navigation input.

In an exemplary embodiment, the medical imaging modality is an ultrasound imaging modality 100. In a representative embodiment, the iteratively reconstructing 512 the high resolution image version 402-408 comprises comparing the high resolution image version 402-408 to the single high resolution image 300 to identify artifacts generated during the iteratively reconstructing 512 the high resolution image version 402-408. In certain embodiments, the iteratively reconstructing 512 the high resolution image version 402-408 comprises removing the identified artifacts from the high resolution image version 402-408. In various embodiments, the method 500 may comprise storing 508, 512 the low resolution cine loop sequence 200 and the high resolution cine loop sequence 400. In an exemplary embodiment, the high resolution cine loop sequence 400 comprises the single high resolution image 300 and the high resolution image version 402-408 of each of the low resolution images 202-208 in the series of sequentially acquired low resolution images of the low resolution cine loop sequence 200. In a representative embodiment, the method 500 may comprise receiving 502 low resolution image acquisition parameters for acquisition of the low resolution cine loop sequence 200. The method 500 may comprise receiving 504 high resolution image acquisition parameters for acquisition of the single high resolution image 300. In certain embodiments, the low resolution image acquisition parameters comprise a low resolution line density parameter that is less than a high resolution line density parameter of the high resolution image acquisition parameters.

Various embodiments provide a system 100 for reconstructing high resolution versions 402-408 of low resolution images 202-208 of a cine loop sequence 200. A medical imaging modality may comprise at least one processor 132,140,150,160 and a display system 134. The at least one processor 132, 140, 160 may be configured to receive a low resolution cine loop sequence 200 comprising a series of sequentially acquired low resolution images 202-208. The at least one processor 132,140,150 may be configured to receive a user input stopping the acquisition of the low resolution cine loop sequence 200. The at least one processor 132, 150, 160 may be configured to receive a single high resolution image 300 in response to the receiving the user input stopping the acquisition of the low resolution cine loop sequence 200. The at least one processor 132,160 may be configured to iteratively reconstruct a high resolution image version 402-408 of each of the low resolution images 202-208 in the series of sequentially acquired low resolution images 200 in reverse, beginning with a last acquired low resolution image 202 and ending with a first acquired low resolution image 208, to generate a high resolution cine loop sequence 400. The high resolution image version 402 of the last acquired low resolution image 202 is reconstructed based on the last acquired low resolution image 202 and the single high resolution image 300. The high resolution image version 404-408 of each of the low resolution images 204-208 prior to the last acquired low resolution image 202 is iteratively reconstructed based on a respective low resolution image 204-208 and the high resolution image version 402-406 of a subsequently acquired low resolution image 202-206 in the series of sequentially acquired low resolution images 200. The at least one processor 132 may be configured to receive a user navigation input selecting a high resolution image version 402-408 from the high resolution cine loop sequence 400. The display system 134 may be configured to present the high resolution image version 402-408 based on the user navigation input.

In a representative embodiment, the medical imaging modality is an ultrasound imaging modality 100. In certain embodiments, the at least one processor 132,160 is configured to compare the high resolution image version 402-408 to the single high resolution image 300 to identify artifacts generated during the iterative reconstruction of the high resolution image version 402-408. In various embodiments, the at least one processor 132, 160 is configured to remove the identified artifacts from the high resolution image version 402-408. In an exemplary embodiment, the imaging modality comprises a data storage medium 138 configured to store the low resolution cine loop sequence 200 and the high resolution cine loop sequence 400. In a representative embodiment, the high resolution cine loop sequence 400 comprises the single high resolution image 300 and the high resolution image version 402-408 of each of the low resolution images 202-208 in the series of sequentially acquired low resolution images of the low resolution cine loop sequence 200. In various embodiments, the at least one processor 132,140 is configured to receive low resolution image acquisition parameters for acquisition of the low resolution cine loop sequence 200. The at least one processor 132, 150 is configured to receive high resolution image acquisition parameters for acquisition of the single high resolution image 300. The low resolution image acquisition parameters comprise a low resolution line density parameter that is less than a high resolution line density parameter of the high resolution image acquisition parameters.

Certain embodiments provide a non-transitory computer readable medium having stored thereon, a computer program having at least one code section. The at least one code section is executable by a medical imaging modality for causing the medical imaging modality to perform steps 500. The steps 500 may comprise acquiring 506 a low resolution cine loop sequence 200 comprising a series of sequentially acquired low resolution images 202-208. The steps 500 may comprise receiving 508 a user input stopping the acquisition of the low resolution cine loop sequence 200. The steps 500 may comprise acquiring 510 a single high resolution image 300 in response to the receiving 508 the user input stopping the acquisition of the low resolution cine loop sequence 200. The steps 500 may comprise iteratively reconstructing 512 a high resolution image version 402-408 of each of the low resolution images 202-208 in the series of sequentially acquired low resolution images 200 in reverse, beginning with a last acquired low resolution image 202 and ending with a first acquired low resolution image 208, to generate a high resolution cine loop sequence 400. The high resolution image version 402 of the last acquired low resolution image 202 is reconstructed based on the last acquired low resolution image 202 and the single high resolution image 300. The high resolution image version 404-408 of each of the low resolution images 204-208 prior to the last acquired low resolution image 202 is iteratively reconstructed based on a respective low resolution image 204-208 and the high resolution image version 402-406 of a subsequently acquired low resolution image 202-206 in the series of sequentially acquired low resolution images 200. The steps 500 may comprise receiving 514 a user navigation input selecting a high resolution image version 402-408 from the high resolution cine loop sequence 400. The steps 500 may comprise causing a display system 134 to present the high resolution image version 402-408 based on the user navigation input.

In various embodiments, the medical imaging modality is an ultrasound imaging modality 100. In certain embodiments, the iteratively reconstructing 512 the high resolution image version 402-408 comprises comparing the high resolution image version 402-408 to the single high resolution image 300 to identify artifacts generated during the iteratively reconstructing 512 the high resolution image version 402-408. In an exemplary embodiment, the iteratively reconstructing 512 the high resolution image version 402-408 comprises removing the identified artifacts from the high resolution image version 402-408. In a representative embodiment, the steps 500 may comprise receiving 502 low resolution image acquisition parameters for acquisition of the low resolution cine loop sequence 200. The steps 500 may comprise receiving 504 high resolution image acquisition parameters for acquisition of the single high resolution image 300. The low resolution image acquisition parameters may comprise a low resolution line density parameter that is less than a high resolution line density parameter of the high resolution image acquisition parameters.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for reconstructing high resolution versions of low resolution images of a cine loop sequence.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
   acquiring, by a medical imaging modality, a low resolution cine loop sequence comprising a series of sequentially acquired low resolution images;
   receiving, by at least one processor, a user input stopping the acquisition of the low resolution cine loop sequence;
   acquiring, by the medical imaging modality, a single high resolution image in response to the receiving the user input stopping the acquisition of the low resolution cine loop sequence;
   iteratively reconstructing, by the at least one processor, a high resolution image version of each of the low resolution images in the series of sequentially acquired low resolution images in reverse, beginning with a last acquired low resolution image and ending with a first acquired low resolution image, to generate a high resolution cine loop sequence, wherein:
      the high resolution image version of the last acquired low resolution image is reconstructed based on the last acquired low resolution image and the single high resolution image, and
      the high resolution image version of each of the low resolution images prior to the last acquired low resolution image is iteratively reconstructed based on a respective low resolution image and the high resolution image version of a subsequently acquired low resolution image in the series of sequentially acquired low resolution images;
   receiving, by the at least one processor, a user navigation input selecting a high resolution image version from the high resolution cine loop sequence; and
   causing a display system to present, by the at least one processor, the selected high resolution image version based on the user navigation input.

2. The method of claim 1, wherein the medical imaging modality is an ultrasound imaging modality.

3. The method of claim 1, wherein the iteratively reconstructing the high resolution image version comprises comparing the high resolution image version to the single high resolution image to identify artifacts generated during the iteratively reconstructing the high resolution image version.

4. The method of claim 3, wherein the iteratively reconstructing the high resolution image version comprises removing the identified artifacts from the high resolution image version.

5. The method of claim 1, comprising storing the low resolution cine loop sequence and the high resolution cine loop sequence.

6. The method of claim 1, wherein the high resolution cine loop sequence comprises the single high resolution image and the high resolution image version of each of the low resolution images in the series of sequentially acquired low resolution images of the low resolution cine loop sequence.

7. The method of claim 1, comprising
   receiving low resolution image acquisition parameters for acquisition of the low resolution cine loop sequence; and
   receiving high resolution image acquisition parameters for acquisition of the single high resolution image.

8. The method of claim 7, wherein the low resolution image acquisition parameters comprise a low resolution line density parameter that is less than a high resolution line density parameter of the high resolution image acquisition parameters.

9. A medical imaging modality comprising:
   at least one processor configured to:
      receive a low resolution cine loop sequence comprising a series of sequentially acquired low resolution images;

receive a user input stopping the acquisition of the low resolution cine loop sequence;

receive a single high resolution image in response to the receiving the user input stopping the acquisition of the low resolution cine loop sequence;

iteratively reconstruct a high resolution image version of each of the low resolution images in the series of sequentially acquired low resolution images in reverse, beginning with a last acquired low resolution image and ending with a first acquired low resolution image, to generate a high resolution cine loop sequence, wherein:

the high resolution image version of the last acquired low resolution image is reconstructed based on the last acquired low resolution image and the single high resolution image, and the high resolution image version of each of the low resolution images prior to the last acquired low resolution image is iteratively reconstructed based on a respective low resolution image and the high resolution image version of a subsequently acquired low resolution image in the series of sequentially acquired low resolution images; and receive a user navigation input selecting a high resolution image version from the high resolution cine loop sequence; and a display system configured to present the selected high resolution image version based on the user navigation input.

10. The medical imaging modality of claim 9, wherein the medical imaging modality is an ultrasound imaging modality.

11. The medical imaging modality of claim 9, wherein the at least one processor is configured to compare the high resolution image version to the single high resolution image to identify artifacts generated during the iterative reconstruction of the high resolution image version.

12. The medical imaging modality of claim 9, wherein the at least one processor is configured to remove the identified artifacts from the high resolution image version.

13. The medical imaging modality of claim 9, comprising a data storage medium configured to store the low resolution cine loop sequence and the high resolution cine loop sequence.

14. The medical imaging modality of claim 9, wherein the high resolution cine loop sequence comprises the single high resolution image and the high resolution image version of each of the low resolution images in the series of sequentially acquired low resolution images of the low resolution cine loop sequence.

15. The medical imaging modality of claim 9, wherein the at least one processor is configured to:

receive low resolution image acquisition parameters for acquisition of the low resolution cine loop sequence; and receive high resolution image acquisition parameters for acquisition of the single high resolution image, wherein the low resolution image acquisition parameters comprise a low resolution line density parameter that is less than a high resolution line density parameter of the high resolution image acquisition parameters.

16. A non-transitory computer readable medium having stored thereon, a computer program having at least one code section, the at least one code section being executable by a machine for causing a medical imaging modality to perform steps comprising:

acquiring a low resolution cine loop sequence comprising a series of sequentially acquired low resolution images;

receiving a user input stopping the acquisition of the low resolution cine loop sequence;

acquiring a single high resolution image in response to the receiving the user input stopping the acquisition of the low resolution cine loop sequence;

iteratively reconstructing a high resolution image version of each of the low resolution images in the series of sequentially acquired low resolution images in reverse, beginning with a last acquired low resolution image and ending with a first acquired low resolution image, to generate a high resolution cine loop sequence, wherein:

the high resolution image version of the last acquired low resolution image is reconstructed based on the last acquired low resolution image and the single high resolution image, and the high resolution image version of each of the low resolution images prior to the last acquired low resolution image is iteratively reconstructed based on a respective low resolution image and the high resolution image version of a subsequently acquired low resolution image in the series of sequentially acquired low resolution images;

receiving a user navigation input selecting a high resolution image version from the high resolution cine loop sequence; and causing a display system to present the selected high resolution image version based on the user navigation input.

17. The non-transitory computer readable medium of claim 16, wherein the medical imaging modality is an ultrasound imaging modality.

18. The non-transitory computer readable medium of claim 16, wherein the iteratively reconstructing the high resolution image version comprises comparing the high resolution image version to the single high resolution image to identify artifacts generated during the iteratively reconstructing the high resolution image version.

19. The non-transitory computer readable medium of claim 18, wherein the iteratively reconstructing the high resolution image version comprises removing the identified artifacts from the high resolution image version.

20. The non-transitory computer readable medium of claim 16, comprising receiving low resolution image acquisition parameters for acquisition of the low resolution cine loop sequence; and receiving high resolution image acquisition parameters for acquisition of the single high resolution image, wherein the low resolution image acquisition parameters comprise a low resolution line density parameter that is less than a high resolution line density parameter of the high resolution image acquisition parameters.

* * * * *